(12) United States Patent
Coelingh Bennink et al.

(10) Patent No.: US 10,179,107 B2
(45) Date of Patent: Jan. 15, 2019

(54) TABLET CONTAINING DEHYDROEPIANDROSTERONE (DHEA)

(75) Inventors: Herman Jan Tijmen Coelingh Bennink, Zeist (NL); Johannes Jan Platteeuw, Boxtel (NL)

(73) Assignee: PANTARHEI BIOSCIENCE B.V., Zeist (NL)

( * ) Notice: Subject to any disclaimer, the term of this patent is extended or adjusted under 35 U.S.C. 154(b) by 0 days.

(21) Appl. No.: 14/233,666

(22) PCT Filed: Jul. 17, 2012

(86) PCT No.: PCT/NL2012/050512
§ 371 (c)(1),
(2), (4) Date: Apr. 3, 2014

(87) PCT Pub. No.: WO2013/012326
PCT Pub. Date: Jan. 24, 2013

(65) Prior Publication Data
US 2014/0235598 A1    Aug. 21, 2014

(30) Foreign Application Priority Data
Jul. 19, 2011    (EP) .................................. 11174451

(51) Int. Cl.
*A61K 9/20* (2006.01)
*A61K 31/567* (2006.01)
*A61K 31/5685* (2006.01)

(52) U.S. Cl.
CPC .......... *A61K 9/2095* (2013.01); *A61K 9/2054* (2013.01); *A61K 9/2077* (2013.01); *A61K 31/567* (2013.01); *A61K 31/5685* (2013.01)

(58) Field of Classification Search
None
See application file for complete search history.

(56) References Cited

U.S. PATENT DOCUMENTS

| 5,725,883 | A * | 3/1998 | Staniforth et al. | ............ 424/489 |
| 6,262,072 | B1 | 7/2001 | Lee | |
| 2005/0137178 | A1 | 6/2005 | Labrie | |

FOREIGN PATENT DOCUMENTS

| CA | 2332767 A1 | 9/2000 |
| DE | 19650352 A1 | 7/1998 |
| EP | 0 429 187 B1 * | 1/1994 |
| GB | 2 240 472 A1 | 8/1991 |
| WO | WO-02/094279 A1 | 11/2002 |
| WO | WO-03/041719 | 5/2003 |
| WO | WO-2004/105694 A2 | 12/2004 |
| WO | WO-2010/145010 A1 | 12/2010 |

OTHER PUBLICATIONS

Shin-Etsu Chemical Co. (Pharmacoat-revised Oct. 2004).*
Bolhuis et al (Eur J Pharmaceut Sci, 1997; 5:63-69).*
Acupuncture Atlanta: "Symphora 60 tablets," Metagenics, 2010, retrieved from the Internet on Sep. 23, 2011—http://www.acuatlanta.net, 2 pgs.
Anonymous: "Allergy Research Group DHEA Micronized Lipid Matrix," Mar. 15, 2011, retrieved from the Internet Sep. 12, 2011—http://www.vitasouth.com, 4 pgs.
Anonymous: "DHEA", lifelinknet.com, 2010, retrieved from the Internet Sep. 12, 2011—http://www.lifelinknet.com/siteResources/Products/DHEA.asp, 2 pgs.
Bergamante, V. et al.. "The Role of Excipients in the Control of Dehydroepiandrosterone Inclusion Complex Delivery," American Journal of Drug Delivery, vol. 4, No. 2, Jan. 1, 2006, pp. 105-112.
International Preliminary Report on Patentability dated Jul. 23, 2013 in Application No. PCT/NL2012/050512.
International Search Report dated Sep. 5, 2012 in Application No. PCT/NL2012/050512.
Mora et al., "Development of a sustained-release matrix tablet formulation of DHEA as ternary complex with alpha-cyclodextrin and glycine," J. Incl Phenon Macrocycl Chem, vol. 57, Feb. 28, 2007, pp. 699-704.
Translation of Decision on Grant issued in co-pending Russian Patent Application No. 2014106066, Mar. 21, 2017.
Translation of Office Action Issued in co-pending Russian Patent Application No. 2014106066, dated Jul. 25, 2016.

* cited by examiner

*Primary Examiner* — Marcos L Sznaidman
*Assistant Examiner* — Rayna Rodriguez
(74) *Attorney, Agent, or Firm* — Gilberto M. Villacorta; Sunit Talapatra

(57) ABSTRACT

The present invention relates to a tablet having a weight of 30-200 mg and consisting of:
   60-100 wt. % of granules consisting of:
      50-90% by weight of the granules of dehydroepiandrosterone (DHEA);
      6-35% by weight of the granules of microcrystalline cellulose;
      0-20% by weight of the granules of one or more other pharmaceutically acceptable granule ingredients; and
   0-40 wt. % of one or more other pharmaceutically acceptable tablet components.
These tablets can suitably be used to orally administer DHEA in dosages of around 50 mg and are sufficiently small to be incorporated in, for instance, ordinary oral contraceptive blister packs.

24 Claims, No Drawings

TABLET CONTAINING DEHYDROEPIANDROSTERONE (DHEA)

CROSS-REFERENCE TO RELATED APPLICATIONS

This application is the National Phase of International Patent Application No. PCT/NL2012/050512, filed Jul. 17, 2012, published as WO 2013/012326, which claims priority to European Application No. 11174451.2, filed Jul. 19, 2011. The contents of these applications are herein incorporated by reference in their entirety.

TECHNICAL FIELD OF THE INVENTION

The present invention relates to a tablet that contains the human androgen dehydroepiandrosterone (DHEA). More particularly, the invention provides a small tablet having a weight of 30-200 mg, said tablet comprising at least 60 wt. % of granules comprising 50-90% DHEA by weight of the granules.

The invention also provides a method of manufacturing the aforementioned tablet.

BACKGROUND OF THE INVENTION

Dehydroepiandrosterone (DHEA), also known as 3-beta-hydroxyandrost-5-en-17-one, dehydroisoandrosterone, trans-dehydroandrosterone, $\Delta^5$-androsten-3-$\beta$-ol-17-one, and prasterone is a naturally occurring intermediate formed in the course of synthesis of various steroids from cholesterol. DHEA is the most abundant steroid hormone in humans and is produced mainly by the adrenal cortex as an inactive sulfate ester (DHEA-S). DHEA production also occurs in the testes, ovaries, and brain.

DHEA has been implicated in a broad range of biological effects in humans and other mammals. It acts on the androgen receptor both directly and through its metabolites, which include androstanediol and androstenedione, which can undergo further conversion to produce the androgen testosterone and the estrogens estrone, estradiol, and estriol.

DHEA has been proposed for use in treating many medical conditions, such as systemic lupus erythematosus, primary adrenal insufficiency, Addison's disease, reduced libido, obesity, osteoporosis, fibromyalgia and benign gynaecological conditions such as endometriosis. It has also been suggested to employ DHEA in female hormonal oral contraceptives with the aim to prevent testosterone loss and maintaining physiological androgen levels (WO 2003/041719). The issue of loss of androgens, especially testosterone, is a potential problem experienced by all women using hormonal oral contraceptives.

DHEA can be administered by different routes. Unlike various other known androgens, DHEA is orally active. Applicant has found that daily administration of DHEA in an oral dosage of around 50 mg to female users of hormonal oral contraceptives normalizes total testosterone completely and free testosterone for at least 50%, without causing excessively high testosterone levels or clinical symptoms of hyperandrogenicity and without increasing estradiol levels. Apart from the ability of DHEA to restore and normalize androgen levels, important significant clinical benefits have been observed on several aspects of sexual function (arousability, responsivity, genital sensation, lubrication), mood and menstrual distress symptoms.

Thus, it would be desirable to include DHEA in, for instance, oral contraceptive tablets. However, oral contraceptive tablets are relatively small, typically having a mass of about 80 mg. Incorporation of about 50 mg DHEA in a tablet of about 80 mg poses a real challenge as in such a tablet DHEA inevitably becomes the main component, leaving very little room for other constituents that are normally used in tablets to enable tabletting, to promote dissolution, to prevent retrogradation etc.

Oral dosage units containing DHEA are known in the art. US 2005/137178 describes a method of treating or reducing the risk of acquiring hypercholesterolemia comprising administering a therapeutically effective amount of a dehydroepiandrosterone. Oral dosage units containing up to 15 wt. % DHEA are described in the examples of this U.S. patent application.

Corvi Mora et al. (*Development of a sustained-release matrix tablet formulation of DHEA as ternary complex with α-cyclodextrin and glycine*, J Incl Phenom Macrocycl Chem (2007) 57, 699-704) describes a sustained release tablet having a weight of 550 mg and containing 25 mg DHEA.

WO 2004/105694 relates to pharmaceutical compositions comprising an active agent; a vitamin E substance; and a surfactant. In the examples a pharmaceutical composition is described that has a total weight of 675 mg and that contains 100 mg DHEA.

WO 2010/145010 is concerned with the reduction or elimination of the incidence of hot flushes, vasomotor symptoms and night sweats by administering a combination of a (i) sex steroid precursor, such as DHEA, and (ii) a selective estrogen receptor modulator or an antiestrogen. The examples of the international application describe a gelatin capsule containing 25 wt. % DHEA.

SUMMARY OF THE INVENTION

The inventors have found a way to produce a tablet that can suitably be used to orally administer DHEA in dosages of around 50 mg and that is sufficiently small to be incorporated in, for instance, ordinary oral contraceptive blister packs.

It was discovered that a granulate with an exceptionally high payload of DHEA can be prepared by wet granulation of a premix of DHEA and microcrystalline celluloses. Furthermore, it was found that this granulate can suitably be incorporated in tablets in very high concentrations of 90 wt. % or more, thereby enabling the manufacture of tablets having a DHEA content of 70 wt. % or more.

Accordingly, the present invention provides a tablet that comprises 60-90 wt. % of a granulate that is made up of 50-90 wt. % DHEA; 6-35 wt. % of microcrystalline cellulose; and optionally up to 20 wt. % of one or more other pharmaceutically acceptable granule ingredients. Besides the granules the tablet may comprise 0-40 wt. % of one or more other pharmaceutically acceptable tablet components.

The tablets of the present invention may suitably be used in oral contraceptives for the prevention of testosterone loss and for maintaining physiological androgen levels. Other clinical benefits for the present tablets include improving sexual function, mood and wellness.

The invention further provides a process of manufacturing the aforementioned tablet, said process comprising the steps of:

providing a dry premix of DHEA, microcrystalline cellulose and optionally one or more other pharmaceutically acceptable granule ingredients;

granulating the dry premix by wetting said premix with an aqueous solution of a binding agent;

drying the wet granules so obtained;

optionally mixing the dried granules with one or more other pharmaceutically acceptable tablet components; and pressing the dried granules or the mixture of dried granules and other tablet components into tablets.

DETAILED DESCRIPTION OF THE INVENTION

One aspect of the invention relates to a tablet having a weight of 30-200 mg, preferably of 60-120 mg, said tablet consisting of:

60-100 wt. % of granules consisting of:
  50-90% by weight of the granules of dehydroepiandrosterone (DHEA);
  6-35% by weight of the granules of microcrystalline cellulose;
  0-20% by weight of the granules of one or more other pharmaceutically acceptable granule ingredients; and
0-40 wt. % of one or more other pharmaceutically acceptable tablet components.

The term "DHEA" as used herein, unless indicated otherwise, refers to dehydroepiandrosterone and pharmaceutically acceptable esters thereof, including DHEA-sulphate.

The term "tablet" as used herein refers to a solid composition that is compressed or otherwise formed into a defined shape and quantity.

The term "granule" as used herein refers to a discrete agglomerate of particles in which the constituent particles are bound together.

The term "microcrystalline cellulose" as used herein refers to a non-fibrous form of cellulose in which the cell wall of the fibers have been broken into fragments, typically ranging in size from a few hundred microns to a few tenths of a micron in length.

The granules comprised in the tablet of the present invention typically have a particle size in the range of 25-500 µm. More preferably, the granules have particle size in the range of 30-350 µm, most preferably in the range of 50-200 µm The present invention offers the advantage that it enables the manufacture of tablets containing at least 40%, even more preferably at least 50% and most preferably at least 55 wt. % of DHEA by weight of the tablet. Typically, the DHEA content of the tablet will not exceed 85 wt. %, most preferably it will not exceed 80 wt. %.

The tablet of the present invention advantageously comprises 20-120 mg, more preferably 35-80 mg and most preferably 40-70 mg DHEA.

The DHEA content of the granules that are comprised within the present tablet preferably lies in the range of 60-85%, more preferably 65-80% by weight of the granules. Most preferably the granules contain 75-80% of DHEA by weight of the granules.

The amount of microcrystalline cellulose contained in the granules preferably lies within the range of 10-25 wt.

Together, DHEA and microcrystalline cellulose preferably constitute at least 85 wt. %, most preferably at least 95 wt. % of the granules.

The granules contained in the present tablet are agglomerates of DHEA particles and particles microcrystalline cellulose.

Surprisingly, it was found that the DHEA contained in the granules has a favourable impact on the processability of these granules. If, for instance, the DHEA in the granules is replaced by microcrystalline cellulose, the resulting granules become very hard and unsuitable for tabletting.

The DHEA contained in the granules typically has a mass weighted average particle size in the range of 1-200 µm, more preferably in the range of 10-100 µm.

The microcrystalline cellulose contained in the granules preferably has a mass weighted average particle size in the range of 25-200 µm, most preferably of 30-100 µm.

The present invention enables the preparation of a tablet that, even if the poorly water-soluble DHEA represents the bulk of the tablet, dissolves swiftly in water. Accordingly, in accordance with a particularly advantageous embodiment, at least 50% of the DHEA contained in the tablet is released within 30 minutes when the tablet is subjected to a dissolution test (USP apparatus II (paddle), 900 ml dissolution medium of a 1% sodium dodecylsulphate solution in water, 75 rpm, T=37.5° C.).

In order to facilitate dissolution, it is preferred that the DHEA-containing granules comprised in the tablet contain 0.5-20 wt. %, preferably 1-10 wt. % of a disintegrating agent. Examples of disintegrating agents that may suitably be employed include carboxymethyl starch salts, carboxymethyl cellulose salts, starch glycolate salts and combinations thereof. Most preferably, the disintegrating agent employed in the present tablet is cross linked sodium carboxymethyl cellulose.

The DHEA-containing granules comprised in the present tablet are suitably produced by wet granulation using an aqueous liquid that contains a binding agent. Accordingly, the granules preferably comprise 1-12 wt. %, most preferably 2-8 wt. % of a binding agent. Examples of binding agents than suitably be employed include hydroxypropyl methyl cellulose, hydroxypropylcellulose, povidone, starch and combinations thereof. Most preferably, the binding agent is hydroxypropyl methyl cellulose.

Besides the DHEA-containing granules, the tablet of the present invention advantageously comprises 10-40 wt. %, most preferably 12-25 wt. % of filler.

The filler is preferably selected from lactose, microcrystalline cellulose, maltodextrine and combinations thereof. According to a particularly preferred embodiment, lactose represents at least 50 wt. %, most preferably at least 70 wt. % of the filler. The filler employed in the tablet preferably has a particle size of 25-200 µm.

The one or more pharmaceutically acceptable tablet components that are optionally present in the tablet preferably include 0.2-3.0%, more preferably 0.5-1.0% lubricant by weight of the tablet. Preferably, said lubricant is magnesium stearate.

As explained herein before the present tablets may suitably be used in oral hormonal contraceptives Such contraceptives usually contain progestogenic and/or estrogenic components. Accordingly, the present tablet advantageously contains an estrogen and/or a progestogen. The estrogen and/or progestogen are advantageously incorporated in the tablet in the form of another granulate, i.e. a granulate other than the DHEA-containing granules.

In accordance with one preferred embodiment of the invention the tablet contains another granulate comprising an estrogen selected from ethinyl estradiol, 17β-estradiol, estetrol and combinations thereof, said estrogen being contained in the tablet in an amount equivalent to 10-40 µg of ethinyl estradiol (p.o.).

In accordance with another preferred embodiment, the tablet contains another granulate comprising a progestogen, said progestogen being contained in the tablet in an amount equivalent to 0.05-2.0 mg levonorgestrel (p.o.).

Another aspect of the present invention relates to a process of manufacturing a tablet as defined herein before, said process comprising the steps of:
- providing a dry premix of DHEA, microcrystalline cellulose and optionally one or more other pharmaceutically acceptable granule ingredients;
- granulating the dry premix by wetting said premix with an aqueous solution of a binding agent;
- drying the wet granules so obtained;
- optionally mixing the dried granules with one or more other pharmaceutically acceptable tablet components; and
- pressing the dried granules or the mixture of dried granules and other tablet components into tablets.

In a preferred embodiment of the present process the dry premix comprises:
- 55-92 wt. % DHEA;
- 7-40 wt. % microcrystalline cellulose; and
- 0-40 wt. % of one or more other pharmaceutically acceptable granule ingredients.

In the present process the premix is preferably wetted with sufficient aqueous solution to provide at least 120% water, more preferably 120-300% water by weight of microcrystalline cellulose.

The wetting of the dry premix may suitably be achieved by e.g. spraying the dry premix with the aqueous solution of a binding agent. Wet granulation techniques are well-know to a person skilled in the pharmaceutical art.

The aqueous solution preferably contains a binding agent as this aids the formation of stable agglomerates. Preferably, the aqueous solution contains 1-20 wt. %, most preferably 3-10 wt. % of a binding agent.

The invention is further illustrated by the following non-limiting examples.

EXAMPLES

Example 1

12.5 grams of raw DHEA (Diosynth) with particles between 1 to 50 μm) was transferred into the bowl of a high shear mixer (MiPro 250, Procept). Next, 7 grams of microcrystalline cellulose (Avicel PH 101, FMC biopolymer, $D_{50}\pm 50$ μm) and 0.5 grams of croscarmellose sodium (Ac-di-sol, FMC biopolymer) were added.

A binder solution containing 10% of HPMC (Pharmacoat 603, Harke group) was prepared and added to the high shear mixer at a rate of 0.3 ml/min.

After addition of 10 ml of binder solution, granulation was stopped. The granules which had a snow-like appearance were dried in an oven at 50° C. for about 1 hour. The dried granules were manually passed through a 0.5 mm sieve. The resulting granules were free flowing.

0.2 mg of magnesium stearate was added to the granulate to create a precompression mixture. Using an single stroke tablet press equipped with 6 mm round punches, tablets of 80 mg were prepared.

Example 2

Example 1 was repeated, except that the amount of DHEA was reduced to 3.5 grams and that granulation was stopped after addition of 9.3 ml binding solution. The granulate so obtained had a snow-like appearance. Tablets of 80 mg could be prepared without difficulty.

Comparative Example A

Example 1 was repeated, except that microcrystalline cellulose was replaced by lactose (Pharmatose 200, DMV-Fonterra) and that granulation was stopped after addition of 9.4 ml of binding solution.

The dried granules so obtained were very hard and could not be broken up during milling over a 500 micron sieve. Due to this, the material was not used for further processing.

Comparative Example B 20 grams of DHEA was transferred into a high shear mixer (MiPro 250, Procept). A binder solution containing 10% of HPMC (3 cP) was prepared and added to the high shear mixer at a rate of 1 ml/min.

The granulation behaviour appeared to be very erratic and the mixture became clearly overwetted after addition of about 5 ml of binder solution.

The granulate consisted of very large balls and much material was sticking to the bowl walls. No effort was made to further process this granulate.

Comparative Example C 18 grams of DHEA was transferred into the bowl of a higher shear mixer (MiPro 250, Procept). 2 grams of pregelatinized starch was added and the two components were briefly blended. Plain water was added to induce granulation. 7.5 ml of water was added before the mixture appeared to be granulated. Much material was sticking to the bowl. The granules were dried in an oven at 60° C.

The granules obtained were very hard and could not be milled over a 500 micron sieve, therefore this product was not used for further processing. . . .

Comparative Example D 12.5 grams of DHEA was transferred into the bowl of a high shear mixer (MiPro 250, Procept). 7 grams of lactose (200 mesh) and 0.5 grams of starch 1500 were added. Plain water was dosed at a rate of 1 ml/min to induce granulation.

After addition of 7.5 ml of water the mixture no granules had formed. After addition of 8.34 ml of water hard pellets were formed and much material was sticking to the bowl walls. No effort was made to further process this material.

Comparative Example E 12.5 grams of DHEA was transferred into the bowl of a high shear mixer (MiPro 250, Procept). 7 grams of lactose (200 mesh) and 0.5 grams of croscarmellose sodium were added. A binder solution containing 10% of HPMC (3 cP) was prepared and added to the high shear mixer at a rate of 1 ml/min. After addition of 7.5 ml of solution, granulation appeared to be completed.

Pellet formation was less compared to comparative example D, but still much material was sticking to the bowl walls.

The granules were dried in an oven at 60° C. The granules obtained were very hard and could not be milled over a 500 micron sieve, therefore this product was not used for further processing.

Comparative Example F 15 grams of microcrystalline cellulose was transferred into the bowl of a high shear mixer (MiPro 250, Procept). A binder solution containing 10% of HPMC (3 cP) was prepared and added to the high shear mixer at a rate of 1 ml/min. After addition of 9 ml of binder solution the granulate had a snow-like appearance and some sticking was observed.

After addition of 14 ml of water (less than 100% by weight) nice round pellets were formed.

The pellets were dried in an oven at 60° C. and after drying they were very hard and slightly yellow coloured.

Example 3

96 grams of DHEA was transferred into the bowl of a high shear mixer (MiPro 900, Procept). Next, 21 grams of microcrystalline cellulose and 3 grams of croscarmellose sodium were added and blended for 1 minute in the high shear mixer.

A binder solution containing 10% of HPMC (3 cP) was prepared and added to the high shear mixer at a rate of 6 ml/min. Granulation went very smooth, no material was sticking to the bowl wall and after addition of 63.4 ml of granulation liquid, granulation was stopped.

The granules were dried in an oven at 40° C. for about 12 hours. The dried granules were manually passed through a 0.5 mm sieve. The yield in granules was 104 grams.

For compression 20 grams of lactose were added and blended for 2 minutes in the high shear mixer. 1 gram of magnesium stearate was added to this mixture and blended for 30 sec in the high shear mixer. Using an single stroke tablet press equipped with 6 mm round punches, tablets of 80 mg were prepared.

The dissolution behaviour of the tablets so obtained was assessed by a dissolution test of 6 individual units, using an USP apparatus II (paddle), 900 ml dissolution medium of a 1% sodium dodecylsulphate solution in water, 75 rpm, T=37.5° C.). It was found that after 10 minutes around 73% and after 20 minutes around 90% of the DHEA contained in the tablet had been released.

Comparative Example G 75 grams of DHEA was transferred into the bowl of a high shear mixer (MiPro 900, Procept). Next, 42 grams of lactose 200 mesh and 3 grams of starch 1500 were added and blended for 1 minute in the high shear mixer. Water was added at a rate of 6 ml/min. After addition of 28.9 ml the granulate starting behaving erratically and granulation had to be stopped to scrape material from the walls. Granulation was restarted but after adding another 4 ml of water, granulation had to be stopped once more to remove the static layer from the bowl wall. At this point the granules still appeared too dry, so an additional 2.5 ml of water was added. The granulate started to form large lumps, so granulation was stopped and the loose contents were transferred onto an aluminum plate and submitted to drying in an oven at 60° C. for 2 hours. 85 grams of very hard granules were obtained.

The granulate was manually passed through a 0.5 mm sieve and blended with 0.9 grams of magnesium stearate. Tablets with a diameter of 6 mm and a tablet weight of 80 mg were prepared with a single stroke tabletting press.

The dissolution behaviour of the tablets so obtained was assessed in the same way as in Example 3. It was found that even after 60 minutes not more than 4% of the DHEA present in the tablet had been released.

The invention claimed is:

1. A tablet having a weight of 30-200 mg, consisting of:
   (a) 60-100 wt. % of granules; and
   (b) 0-40 wt. % of one or more other pharmaceutically acceptable tablet components;
   wherein the granules consist of:
   (i) 50-90 wt. % of dehydroepiandrosterone (DHEA);
   (ii) 6-35 wt. % of microcrystalline cellulose;
   (iii) 1-12 wt. % of binding agent; and
   (iv) 0-20 wt. % of one or more other pharmaceutically acceptable granule ingredients;
   wherein the tablet is manufactured by a process comprising:
   (1) granulating a dry premix comprising DHEA and microcrystalline cellulose by wetting the premix with an aqueous solution of the binding agent;
   (2) drying the wet granules so obtained;
   (3) optionally mixing the dried granules with one or more other pharmaceutically acceptable tablet components; and
   (4) pressing the dried granules or the mixture of dried granules and the one or more other pharmaceutically acceptable tablet components into tablets.

2. The tablet according to claim 1, wherein the tablet has a weight of 60-120 mg.

3. The tablet according to claim 1, wherein the DHEA is present in the tablet in an amount of 40-85% by weight of the tablet.

4. The tablet according to claim 3, the DHEA is present in the tablet in an amount of 50-80% by weight of the tablet.

5. The tablet according to claim 1, wherein the DHEA is present in the granules in an amount of 60-85% by weight of the granules.

6. The tablet according to claim 1, wherein the microcrystalline cellulose is present in the granules in an amount of 10-25% by weight of the granules.

7. The tablet according to claim 1, wherein the pharmaceutically acceptable tablet component is a disintegrating agent and is present in an amount of 0.5-20% by weight of the granules.

8. The tablet according to claim 7, wherein the disintegrating agent is present in the granules in an amount of 1-10% by weight of the granules.

9. The tablet according to claim 7, wherein the disintegrating agent is selected from the group consisting of carboxymethyl starch salt, carboxymethyl cellulose salt, starch glycolate salt and combinations thereof.

10. The tablet according to claim 1, wherein the binding agent is present in the granules in an amount of 2-8% by weight of the granules.

11. The tablet according to claim 1, wherein the binding agent is selected from hydroxypropyl methyl cellulose, hydroxypropylcellulose, povidone, starch and combinations thereof.

12. The tablet according to claim 1, wherein the one or more other pharmaceutically acceptable tablet components comprises 10-40% of filler by weight of the tablet.

13. The tablet according to claim 12, wherein the one or more other pharmaceutically acceptable tablet components comprises 12-25% of filler by weight of the tablet.

14. The tablet according to claim 12, wherein the filler is selected from the group consisting of lactose, microcrystalline cellulose, maltodextrine and combinations thereof.

15. The tablet according to claim 1, wherein the tablet contains another granulate comprising a progestogen, said progestogen being contained in the tablet in an amount equivalent to 0.05-2.0 mg levonorgestrel (p.o.).

16. The tablet according to claim 1, wherein the dried granules have a particle size of 25-500 μm.

17. The tablet according to claim 1, wherein the DHEA has a mass weighted average particle size in the range of 1-200 μm.

18. The tablet according to claim 1, wherein the microcrystalline cellulose has a mass weighted particle size in the range of 25-200 μm.

19. The tablet according to claim 1, wherein the one or more other pharmaceutically acceptable tablet components include a lubricant in an amount of 0.2-3.0% by weight of the tablet.

20. The tablet according to claim 19, wherein the one or more other pharmaceutically acceptable tablet components include a lubricant in an amount of 0.2-1.0% by weight of the tablet.

21. The tablet according to claim 19, wherein the lubricant is magnesium stearate.

22. The tablet according to claim 1, wherein the combination of DHEA and microcrystalline cellulose constitutes at least 85% by weight of the granules.

23. The tablet according to claim 1, wherein the one or more pharmaceutically acceptable granule ingredient is present in an amount of less than 20%.

24. The tablet according to claim 23, wherein the dry premix comprises DHEA, microcrystalline cellulose, and one or more pharmaceutically acceptable granule ingredients.

* * * * *